(12) United States Patent
Porges et al.

(10) Patent No.: US 11,389,106 B2
(45) Date of Patent: Jul. 19, 2022

(54) NON-INVASIVE DIAGNOSTIC BIOMARKER FOR PANCREATIC ISLET POPULATIONS

(71) Applicants: University of Florida Research Foundation, Incorporated, Gainesville, FL (US); Johns Hopkins University, The, Baltimore, MD (US)

(72) Inventors: Eric C. Porges, Gainesville, FL (US); Damon Lamb, Gainesville, FL (US); Martha Campbell Thompson, Micanopy, FL (US); Richard Edden, Baltimore, MD (US)

(73) Assignees: University of Florida Research Foundation, Incorporated, Gainesville, FL (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/756,489

(22) PCT Filed: Oct. 17, 2018

(86) PCT No.: PCT/US2018/056287
§ 371 (c)(1),
(2) Date: Apr. 16, 2020

(87) PCT Pub. No.: WO2019/079449
PCT Pub. Date: Apr. 25, 2019

(65) Prior Publication Data
US 2020/0300793 A1  Sep. 24, 2020

Related U.S. Application Data

(60) Provisional application No. 62/573,281, filed on Oct. 17, 2017.

(51) Int. Cl.
*A61B 5/00* (2006.01)
*A61K 31/155* (2006.01)
(Continued)

(52) U.S. Cl.
CPC .............. *A61B 5/425* (2013.01); *A61B 5/055* (2013.01); *A61K 31/155* (2013.01); *A61K 38/28* (2013.01);
(Continued)

(58) Field of Classification Search
CPC ...... A61B 5/425; A61B 5/055; A61K 31/155; A61K 38/28; G01R 33/485; G01R 33/3415; G01R 33/4616
See application file for complete search history.

(56) References Cited

U.S. PATENT DOCUMENTS

2015/0153324 A1  6/2015  Mun et al.
2016/0377639 A1* 12/2016  Bahado-Singh ....... G01N 33/50
                                                                514/7.7

FOREIGN PATENT DOCUMENTS

WO   WO 2016/174425 A1   11/2016

OTHER PUBLICATIONS

PCT/US2018/056287, Dec. 11, 2018, International Search Report and Written Opinion.
(Continued)

*Primary Examiner* — Joel Lamprecht
(74) *Attorney, Agent, or Firm* — Wolf, Greenfield & Sacks, P.C.

(57) ABSTRACT

Aspects of the disclosure relate to systems and methods for obtaining and interpreting magnetic resonance spectroscopy (MRS) data obtained from the pancreas of a subject. In some embodiments, systems and methods of the disclosure relate to analyzing MRS spectra of metabolites, for example y-Aminobutyric acid (GABA), to assess pancreatic islet density and function in a subject. In some embodiments, systems and methods described by the disclosure are useful for the diagnosis and/or treatment of diseases associated with impaired pancreatic function, for example diabetes.

18 Claims, 2 Drawing Sheets

(51) Int. Cl.
 A61K 38/28 (2006.01)
 G01R 33/485 (2006.01)
 A61B 5/055 (2006.01)
 G01R 33/46 (2006.01)
 G01R 33/3415 (2006.01)
(52) U.S. Cl.
 CPC ........ G01R 33/485 (2013.01); G01R 33/3415 (2013.01); G01R 33/4616 (2013.01)

(56) References Cited

OTHER PUBLICATIONS

PCT/US2018/056287, Apr. 30, 2020, International Preliminary Report on Patentability.
International Search Report and Written Opinion for Application No. PCT/US2018/056287, dated Dec. 11, 2018.
International Preliminary Report on Patentability for Application No. PCT/US2018/056287, dated Apr. 30, 2020.
Begovatz et al., Pancreatic adipose tissue infiltration, parenchymal steatosis and beta cell function in humans. Diabetologia. Jul. 2015;58(7):1646-55. doi: 10.1007/s00125-015-3544-5. Epub Mar. 5, 2015.
Edden et al., Measuring T2 in vivo with J-difference editing: application to GABA at 3 Tesla. J Magn Reson Imaging. Jan. 2012;35(1):229-34. doi: 10.1002/jmri.22865. Epub Nov. 1, 2011.
Porges et al., Frontal Gamma-Aminobutyric Acid Concentrations Are Associated With Cognitive Performance in Older Adults. Biol Psychiatry Cogn Neurosci Neuroimaging. Jan. 2017;2(1):38-44. doi: 10.1016/j.bpsc.2016.06.004.
Soltani et al., GABA exerts protective and regenerative effects on islet beta cells and reverses diabetes. Proc Natl Acad Sci USA. Jul. 12, 2011;108(28):11692-7. doi: 10.1073/pnas.1102715108. Epub Jun. 27, 2011.

* cited by examiner

NON-INVASIVE DIAGNOSTIC BIOMARKER FOR PANCREATIC ISLET POPULATIONS

RELATED APPLICATIONS

This Application is a national stage filing under 35 U.S.C. § 371 of international PCT application, PCT/US2018/056287, filed Oct. 17, 2018, which claims priority under 35 U.S.C. § 119(e) to U.S. Provisional Patent Application Serial Number, U.S. Ser. No. 62/573,281, filed Oct. 17, 2017, the entire contents of each of which are incorporated herein by reference.

GOVERNMENT SUPPORTED RESEARCH

This invention was made with government support under EB015909, EB016089, AA025306, TR001429, TR001427, OD023861, DK101120, DK104155 awarded by the National Institutes of Health. The government has certain rights in the invention.

BACKGROUND

Proton Magnetic resonance spectroscopy (1H-MRS) is an analytical technique that is often used to detect and quantify metabolic changes in vivo in a subject, for example in the brain if a subject. One advantage of 1H-MRS is that it is a non-invasive technique and does not require the use of ionizing radiation. However, the use of 1H-MRS to study metabolites in organs other than the brain faces many challenges, such as adequate signal acquisition, localization of 1H-MR spectra to the desired organ, and complications related to interpreting spectra obtained from different internal structures within a target organ.

SUMMARY

Aspects of the disclosure relate to systems and methods for obtaining and interpreting 1H-MRS data obtained from the pancreas of a subject. The disclosure is based, in part, on the surprising discovery that pancreatic islet function can be characterized using 1H-MRS spectra of certain metabolites (e.g., γ-Aminobutyric acid, GABA and/or glutamate, Glx) that have been acquired from a subject and processed using methods described herein. In some embodiments, systems and methods described by the disclosure are useful for diagnosing and/or treating a subject having or suspected of having a disease associated with impaired pancreatic function, for example diabetes (e.g., type 1 diabetes).

In some aspects, the disclosure provides a method for detecting and/or quantifying GABA in a non-CNS tissue of a subject (e.g., the pancreas of a subject), the method comprising acquiring a plurality of proton magnetic resonance (1H-MR) spectra using a high-field (e.g., greater than or equal to 3 Tesla (T)) magnetic resonance imaging apparatus and, optionally, quantifying GABA concentration in the subject based upon the peak amplitude of a selected spectrum (or spectra) relative to at least one internal reference signal (e.g., spectrum) obtained from the subject.

In some aspects, the disclosure provides a method for detecting and/or quantifying GABA in the pancreas of a subject, the method comprising acquiring a plurality of proton magnetic resonance (1H-MR) spectra from a multi-channel receiver array placed around the torso of a subject; performing subtractive J-difference editing on the 1H-MR spectrum obtained from each channel of the receiver array to produce edited difference spectra by selecting from one or more channels of the receiver array; and, optionally, quantifying GABA concentration in the subject based upon the 3.0 ppm peak amplitude of the selected difference spectra relative to at least one internal reference signal (e.g., spectrum) obtained from the receiver array.

In some embodiments, the plurality of 1H-MR spectra are acquired using a magnetic field strength between 0.2 and 12 Tesla (T). In some embodiments, the plurality of 1H-MR spectra are acquired using a magnetic field strength between 1 and 3 T.

In some embodiments, acquisition of the plurality of 1H-MR spectra comprises a single voxel spectroscopy (SVS) pulse acquisition sequence. In some embodiments, the SVS pulse acquisition sequence comprises a point-resolved spectroscopy (PRESS) acquisition sequence.

In some embodiments, the echo time (TE) of the PRESS acquisition sequence is between 50 ms and 100 ms. In some embodiments, the TE is between 67 ms and 80 ms, optionally wherein the TE is 68 ms.

In some embodiments, acquisition of the plurality of 1H-MR spectra comprises administering one or more chemical-shift-selective editing pulses (e.g., J-difference editing pulses). In some embodiments, the chemical-shift-selective editing pulses are applied at a chemical shift between −2.7 ppm and −2.8 ppm relative to water resonance of the subject. In some embodiments, chemical-shift-selective editing pulses comprise a Mescher-Garwood (MEGA) refocusing pulse sequence. In some embodiments, a MEGA refocusing pulse sequence is between 10 milliseconds (ms) and about 25 milliseconds (ms). In some embodiments, a MEGA refocusing pules is 14 milliseconds (ms).

In some embodiments, the acquiring step is repeated between 100 and 1000 times. In some embodiments, the repetition time (TR) between acquisitions is between 500 milliseconds and 10 seconds.

In some embodiments, the subject is holding their breath during each acquisition of 1H-MR spectrum. In some embodiments the subject has exhaled before holding their breath.

In some embodiments, the multi-channel receiver array comprises at least four channels, at least eight channels, or at least 16 channels. In some embodiments, the multi-channel receiver array is a phased multi-channel receiver array.

In some embodiments, at least four channels of the multi-channel receiver array are positioned to acquire spectra in a position anterior to the subject. In some embodiments, at least four channels of the multi-channel receiver array are positioned to acquire spectra in a position posterior to the subject.

In some embodiments, eight channels of the multi-channel receiver array are positioned to acquire spectra in a position anterior to the subject and eight channels of the multi-channel receiver array are positioned to acquire spectra in a position posterior to the subject.

In some embodiments, at least one channel of the multi-channel receiver array acquires 1H-MR spectra from a voxel within the pancreas of the subject. In some embodiments, a voxel is of sufficient size to encompass the entire pancreas of a subject. In some embodiments, the voxel ranges from about 1 $cm^3$ to about 250 $cm^3$.

In some embodiments, a subject has a mechanically-restrained pancreas.

In some embodiments, concentration of GABA (cGABA) is quantified using the following equation:

$$c_{GABA} = c_{ref} \frac{S_{GABA}}{S_{ref}} R\kappa$$

where $C_{ref}$ is the concentration of the reference signal, $S_{GABA}$ and $S_{ref}$ are the signal integrals of the GABA and reference signals respectively, R is a term to correct for differential relaxation of GABA and reference signals and κ is a constant to adjust for editing efficiency.

In some aspects, the disclosure provides a method for identifying compromised pancreatic islet function in a subject, the method comprising: quantifying a GABA concentration of the subject using a method as described by the disclosure; comparing the GABA concentration in the subject to a reference standard; and, determining that pancreatic islet function of the subject is compromised if the concentration of GABA in the subject is lower than the reference standard.

In some embodiments, a reference standard comprises a GABA concentration obtained from a healthy subject, for example a subject that does not have compromised pancreatic islet function (e.g., a subject that does not have type 1 diabetes).

In some embodiments, methods described by the disclosure further comprise administering a therapeutic agent to a subject if the subject has been determined to have compromised pancreatic islet function.

In some aspects, the disclosure provides a method for treating diabetes in a subject, the method comprising administering a therapeutic agent to the subject, wherein the subject has been determined to have compromised pancreatic islet function by a method as described by the disclosure.

In some embodiments, compromised pancreatic islet function is a result of a subject having diabetes. In some embodiments, diabetes is type 1 diabetes. In some embodiments, the diabetes is type 2 diabetes.

In some embodiments, a type 1 diabetes therapeutic agent is insulin, insulin degludec, insulin isophane, insulin glulisine, insulin lispro, insulin aspart, glargine, detemir, or any combination thereof. In some embodiments, a type 2 diabetes therapeutic agent is metformin, a sulfonylurea, a DPP-4 inhibitor, a glucagon-like peptide (e.g., an incretin mimetic), a thiazolidinedione, an alpha-glucosidase inhibitor (e.g., acarbose, miglitol), a sodium glucose transporter (SGLT) 2 inhibitor, or any combination thereof.

BRIEF DESCRIPTION OF DRAWINGS

FIG. 1A shows editing pulses applied at 1.9 ppm suppress ("ON") the GABA contribution to the 3 ppm glycine/GABA (GLX/GABA) peaks, which are revealed through the difference ("DIFF") between the "ON" and "OFF" spectra. FIG. 1B shows the impact of the 1.9 ppm editing pulse on the 3 ppm peaks.

DETAILED DESCRIPTION

Figure 1A:
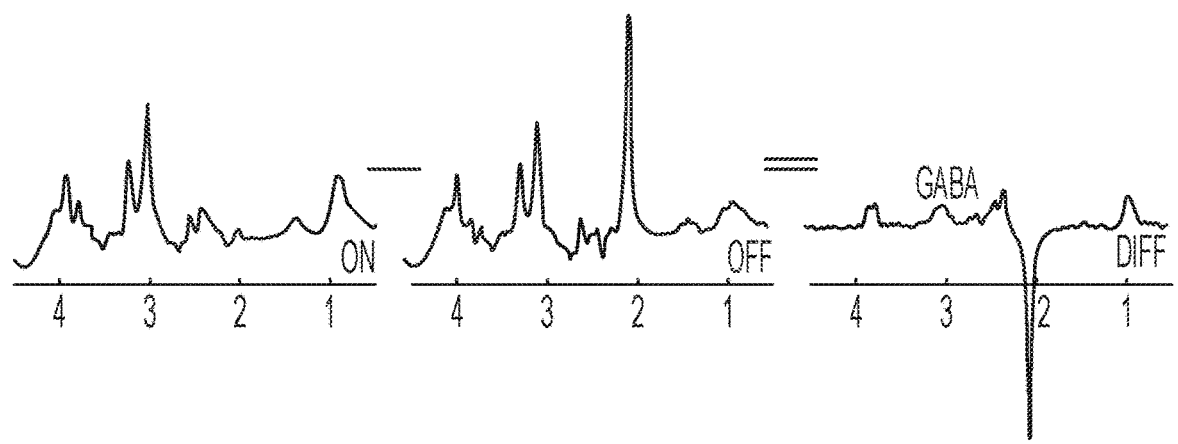
FIGS. 1A-1B shows schematic spectra of a J-difference editing (MEGA-PRESS) approach to MRS measurement of GABA.

Aspects of the disclosure relate to methods and compositions for the detection of certain metabolites (e.g., gluta-mate, GABA) in non-CNS tissue, for example pancreatic tissue. The disclosure is based, in part, on the discovery that pancreatic islet function can be characterized using 1H-MRS spectra of certain metabolites (e.g., γ-Aminobutyric acid, GABA) that have been acquired from a subject and processed using methods described herein. Accordingly, systems and methods described by the disclosure are useful, in some embodiments, for diagnosing and/or treating a subject having or suspected of having a disease associated with impaired pancreatic function, for example diabetes (e.g., type 1 diabetes).

In some aspects, the disclosure provides a method for detecting and/or quantifying y-Aminobutyric acid (GABA) in the pancreas of a subject, the method comprising acquiring a plurality of proton magnetic resonance (1H-MR) spectra from a multi-channel receiver array placed in proximity to (e.g., around) the torso of a subject; performing subtractive J-difference editing on the 1H-MR spectrum obtained from each channel of the receiver array to produce edited difference spectra by selecting from one or more channels of the receiver array; and, optionally, quantifying GABA concentration in the subject based upon the 3.0 ppm peak amplitude of the selected difference spectra relative to at least one internal reference signal (e.g., spectrum) obtained from the receiver array.

Nuclear Magnetic Resonance Spectroscopy (MRS)

Generally, the disclosure relates to methods for analyzing an analyte (e.g., GABA, creatine, etc.) in non-CNS tissue using nuclear magnetic resonance spectroscopy (NMRS or MRS). MRS is an analytical technique which uses strong magnetic fields and radiofrequency waves to determine the biophysical characteristics of molecules, such as small molecules, nucleic acids, peptides and proteins. Typically, MRS measurements are obtained by a magnetic resonance imaging system that generally comprises a strong magnet, a radiofrequency (RF) transmitting coil, a radiofrequency (RF) receiving coil, and one or more gradient coils that are connected to a control module (e.g., comprising one or more computers). MR spectra may be obtained by measuring the resonance frequencies of one or more various isotopes within a subject, for example $^1H$, $^{31}P$, $^{19}F$, $^{13}C$, or $^{23}Na$. Clinical applications of 1H-MRS are generally described, for example by Van der Graaf, Eur. Biophys J. 2010 March; 39(4): 527-540, the entire contents of which are incorporated herein by reference.

Acquisition of 1H-MRS Spectra

Acquisition of 1H-MR spectra relies on the generation of a magnetic field, which is usually measured in Tesla (T) units. Generally, clinical MRS is performed using magnetic fields with a strength greater than 1.5 T. In some embodiments of methods described herein, a plurality of proton magnetic resonance (1H-MR) spectra are acquired from a subject at a magnetic field strength between 0.2 T and 12 T. In some embodiments, 1H-MR spectra are acquired at a magnetic field strength between 1 T and 3 T, between 1.5 T and 5 T, or between 3 T and 9 T. In some embodiments, 1H-MR spectra are acquired at a magnetic field strength of 3 T.

In some embodiments, 1H-MR spectra are acquired using single voxel spectroscopy (SVS). As used herein, the term "single voxel spectroscopy" refers to a MRS acquisition technique that acquires a signal (e.g., a radiofrequency signal or spectrum) from a three-dimensional volume of tissue (e.g., a voxel). Generally, each plane (e.g., X, Y, or Z) of a voxel can be between about 1 μm³ and 500 cm³ (e.g., any volume between 1 cm³ and 500 cm³, inclusive). In some embodiments, each plane (e.g., X, Y, or Z) of a voxel is between about 10 cm³ to about 250 cm³ (e.g., any volume between 10 and 250 cm³). In some embodiments, each plane (e.g., X, Y, or Z) of a voxel is between about 1.0 cm³ to about 5 cm³. In some embodiments, a voxel is about 2.5 cm³×2.5 cm³×5.0 cm³. In some embodiments, a voxel is of sufficient size to encompass the entire pancreas of a subject.

Aspects of the disclosure relate to measurement of GABA in the pancreas of a subject. Thus, in some embodiments, a voxel measured by SVS is located in a non-CNS tissue of a subject (e.g., a mammal, such as a human, non-human primate, rodent, mouse, etc.). In some embodiments, a voxel is located in pancreatic tissue of the subject. In some embodiments, a voxel measured by SVS encompasses beta cells of the subject. In some embodiments, the beta cells comprise GABA. In some embodiments a voxel encompasses only pancreatic cells and structures of a subject (e.g., does not encompass tissue other than pancreatic tissue).

Generally, 1H-MR signals are acquired by exciting the protons within a given sample (e.g., a voxel) and measuring the amount of magnetization using a radiofrequency receiver. In some aspects, the disclosure relates to the discovery that certain combinations of pulse acquisition sequences result in acquisition of 1H-MR spectra (e.g., a GABA peak) from pancreatic tissue of a subject. As used herein, the term "pulse acquisition sequence" refers to a series (e.g., 1, 2, 3, 4, 5, 6, 7, 8, 9, 10, or more) of radiofrequency pulses that are passed through a subject to one or more radiofrequency receivers in order to generate an MRS spectrum.

As used herein, the term "chemical-shift-selective editing pulse" refers to a radiofrequency pulse, or sequence of pulses (e.g., 1, 2, 3, 4, 5, or more, radiofrequency pulses delivered to a sample with a fixed time period), that induces a change in resonance frequency of a particular target analyte (e.g., glutamate, GABA, etc.) relative to other analytes in a sample, thereby increasing the signal-to-noise ratio of the target analyte relative to other analytes in a sample (e.g., water, fat, creatine, etc.). Examples of chemical-shift-selective editing pulses include but are not limited to water suppression editing pulses (e.g., chemical-shift-selective, CHESS pulses), Stimulated Echo Acquisition Mode (STEAM pulses), Point-Resolved Spectroscopy (PRESS) editing pulses, J-difference editing pulses (e.g., MEGA), etc.

In some embodiments, a chemical-shift-selective editing pulse comprises a point-resolved spectroscopy (PRESS) acquisition sequence. In some embodiments, a PRESS sequence comprises, in the following order, a first 90° pulse, a first 180° pulse, and a second 90° pulse.

The echo time (TE) of a chemical-shift-selective editing pulse (e.g., a PRESS pulse sequence) can vary. Without wishing to be bound by any particular theory, the long echo time (TE) used in PRESS sequences (e.g., relative to the TE of other acquisition pulse sequences) increases signal-to-noise ratio for detection of certain analytes (e.g., glutamate, GABA, etc.) by reducing the number of detectable peaks in 1H-MR spectra acquired from a voxel of interest. As used herein, the term "echo time" or "TE" refers to the amount of time a magnetized proton (e.g., a proton in an analyte) is in the transverse plane after an excitation before signal readout. In some embodiments, the echo time (TE) of a PRESS sequences ranges from about 10 milliseconds (ms) to about 500 ms. In some embodiments, the echo time (TE) of a PRESS sequences ranges from about 10 milliseconds (ms) to about 100 ms (e.g., about 10 ms, about 20 ms, about 30 ms, about 40 ms, about 50 ms, about 60 ms, about 70 ms, about 80 ms, about 90 ms, or about 100 ms). In some embodiments the TE of a PRESS sequence ranges from about 67 ms to about 80 ms (e.g., 67 ms, 68 ms, 69 ms, 70 ms, 71 ms, 72 ms, 73 ms, 74 ms, 75 ms, 76 ms, 77 ms, 78 ms, 79 ms or 80 ms).

The disclosure is based, in part, on the use of certain chemical-shift-selective editing pulses (e.g., J-difference editing pulses) that separate or prevent formation of signal multiplets (e.g., doublets, triplets, etc.) in spectra acquired from a voxel. In some embodiments of methods described herein, the chemical-shift-selective editing pulse is a J-difference editing pulse. Examples of J-difference editing pulses (e.g., J-difference editing pulse sequences) include but are not limited to Mescher-Garwood PRESS (MEGA-PRESS), band-selective inversion with gradient dephasing (BASING), etc. In some embodiments, a chemical-shift-selective editing pulse is a MEGA-PRESS pulse sequence.

As used herein "MEGA-PRESS" refers to a J-difference editing pulse sequence described, for example by Mescher et al. (1998) *NMR Biomed.* 11(6):266-72, the entire contents of which are incorporated herein by reference. In some embodiments, a MEGA-PRESS editing pulse sequence comprises one or more (e.g., 1, 2, 3, etc.) editing radiofrequency pulses applied at a chemical-shift that is between about −2.9 ppm and about −2.8 ppm relative to an internal reference signal (e.g., a water signal). In some embodiments, a MEGA-PRESS editing pulse sequence is applied to the 1.9 ppm GABA peak of a 1H-MR spectrum.

As used herein an "internal reference signal" refers to a known chemical peak present in a 1H-MR spectrum, from which chemical shift of other analytes is measured, typically in parts per million (ppm) or in Hertz (Hz). Generally, MRS internal reference standards are known in the art, and include water, creatine, choline, etc. In some embodiments of methods described herein, the internal reference standard is a water signal (e.g., the resonance of water in a particular voxel).

Generally, a plurality of 1H-MR spectra are obtained from a voxel of interest (e.g., a particular voxel selected within a subject) by repeating the acquiring step of methods described herein. In some embodiments, the acquisition step is repeated between 100 and 1000 times (e.g., any integer between 100 and 1000, inclusive). In some embodiments, the acquisition step is repeated about 100, about 125, about 150, about 175, about 200, about 250, about 300, about 450, about 500, about 750, or 1000 times. In some embodiments, each repetition of the acquisition step comprises a MEGA-PRESS pulse sequence.

The repetition time between acquisition steps can vary. As used herein, the term "repetition time" or "TR" refers to the amount of time between each acquisition set of a method as described herein. In some embodiments, the repetition time (TR) between each acquisition step of a method described herein ranges from about 500 milliseconds (ms) to about 10 seconds. In some embodiments, the repetition time (TR) between each acquisition step of a method described herein ranges from about 10 seconds to about 5 seconds, about 8 seconds to about 2 seconds, about 3 seconds to about 750 ms, or about 1 second to about 500 ms.

In some aspects, the disclosure relates to the discovery that obtaining 1H-MR spectra from a multi-channel receiver array around the torso of a subject allows for the detection of GABA in the pancreas of the subject. As used herein, a "multi-channel receiver array" refers to a radiofrequency (RF) receiver array that comprises two or more receivers configured to detect a 1H-MR signal (e.g., radiofrequency signal) from one or more voxels of a subject. The disclosure is based, in part, on the discovery that MRS methods utilizing certain arrangements of receiver arrays (e.g., positioning of receivers around the torso of a subject), in combination with particular acquisition and editing pulse sequences (e.g., MEGA-PRESS), result in detection of 1H-MR spectra comprising quantifiable GABA peaks from non-CNS tissue (e.g., from one or more voxels comprising or consisting of pancreatic tissue or pancreatic cells).

In some embodiments, a multi-channel receiver array comprises two or more (e.g., 2, 3, 4, 5, 6, 7, 8, 9, 10, 11, 12, 13, 14, 15, 16, 17, 18, 19, 20, or more) channels. In some embodiments, a multi-channel receiver array comprises 16 channels. The arrangement of channels of a multi-channel receiver array can vary (e.g., positioning of the channels of an array can vary with respect to a subject). In some embodiments, at least eight channels (e.g., 8, 9, 10, 11, 12, 13, 14, 15, 16, or more channels) of an array are positioned to acquire spectra from a position anterior to a subject. For example, in some embodiments, at least eight channels of a multi-channel receiver array are placed in front (e.g., anterior) of a subject's torso. In some embodiments, at least eight channels of a multi-channel receiver array are placed in behind (e.g., anterior to) a subject's torso. In some embodiments, the receiver is placed 0.25 inches, 0.5 inches, 0.75 inches, 1 inch, 1.5 inches, 5 inches, 12 inches, 1.5 feet or 2 feet in front of a subject. In some embodiments, the receiver is placed 0.25 inches, 0.5 inches, 0.75 inches, 1 inch, 1.5 inches, 5 inches, 12 inches, 1.5 feet or 2 feet in front of a subject.

GABA and Pancreatic Function

In some aspects, the disclosure relates to the use of magnetic resonance spectroscopy methods described herein for detecting the presence (or absence) of GABA and/or the concentration of GABA in a non-CNS tissue (e.g., pancreas) of a subject. As used herein, "γ-Aminobutyric acid (GABA)" refers to an amino acid having the following structure,

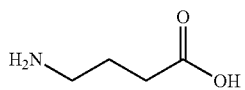

that binds to its cognate receptors (e.g., $GABA_A$ and $GABA_B$) and typically functions, in vertebrates, as an inhibitory neurotransmitter in the central nervous system (CNS). However, GABA is also present in several vertebrate (e.g., mammalian) peripheral tissues, for example, the intestines, stomach, kidneys, pancreas, fallopian tubes, uterus, ovaries, testes, kidneys, bladder, lungs, and liver.

Previously described techniques for quantifying GABA in a subject using MRS are focused on the central nervous system (CNS) of the subject. A "subject" generally refers to any mammalian organism that can be subjected to magnetic responance imaging, including but not limited to humans, non-human primates (e.g., monkeys, chimpanzees, etc.) rodents (e.g., mice, rats, guinea pigs, hamsters etc.), dogs, cats, cows, etc. In some embodiments, a subject is a human subject. In some embodiments, a subject has or is suspected of having a disease associated with compromised pancreatic function, for example diabetes (e.g., type 1 or type 2 diabetes).

A subject "having" a disease is a subject who exhibits signs and symptoms of a disease (e.g., diabetes) and has been diagnosed by a medical doctor, for example after a confirmatory diagnostic test (e.g., a blood glucose test in the case of diabetes). A subject "suspected of having a disease" is a subject who exhibits signs and symptoms of a disease (e.g., diabetes) but has not been diagnosed by a medical doctor and/or has not been administered a diagnostic test. In some embodiments, a subject suspected of having diabetes is a pre-diabetic subject, for example as described in Gundy (2012) *J Am Coll Cardiol.* 59(7):635-43.

In some embodiments, methods described herein detect the presence (or absence) of GABA in non-CNS tissue of a subject. As used herein "non-CNS tissue" refers to tissue and cells of a subject that are not part of the central nervous system (e.g., brain, spinal cord, cerebrospinal fluid, etc.) of a subject. In some embodiments, non-CNS tissue is pancreatic tissue or pancreatic cells.

In some embodiments, GABA is present in beta cells (β cells) of the pancreas. β cells, which form a large percentage of the cells in pancreatic islets, control the production and release of insulin, and therefore play an important role in diseases associated with regulation of blood glucose concentrations (e.g., diabetes mellitus, such as type 1 diabetes, type 2 diabetes, gestational diabetes, etc.). Without wishing to be bound by any particular theory, the disclosure is based, in part, on the discovery that quantification of GABA concentrations in the pancreas (e.g., β cells of the pancreas) of a subject using 1H-MRS is indicative of pancreatic islet function of the subject, and thus is useful for determining whether a subject has or is at risk of having a disease characterized by compromised pancreatic islet function. Various methods of determining the concentration or amount of an analyte based upon a MRS spectrum are know in the art. In some embodiments, GABA concentration in a subject is determined using the following equation:

$$c_{GABA} = c_{ref} \frac{S_{GABA}}{S_{ref}} R\kappa$$

where $C_{ref}$ is the concentration of the reference signal, $S_{GABA}$ and $S_{ref}$ are the signal integrals of the GABA and reference signals respectively, R is a term to correct for differential relaxation of GABA and reference signals and κ is a constant to adjust for editing efficiency.

In some aspects, the disclosure relates to methods of identifying and/or treating compromised pancreatic function (e.g., a disease associated with compromised pancreatic function, such as diabetes) in a subject. In some embodiments, the disease is type 1 diabetes. In some embodiments, the disease is type 2 diabetes. In some embodiments, methods of identifying a subject having compromised pancreatic function comprise the steps of quantifying the amount (e.g., concentration) of GABA in the pancreas of the subject (e.g., using methods described herein), comparing the GABA amount (or concentration) to a reference standard, and determining that pancreatic islet function of the subject is compromised if the amount of GABA in the subject is lower than the reference standard.

As used herein, "reference standard" refers to an amount (e.g., concentration) of GABA quantified from a healthy subject (e.g., a subject not having compromised pancreatic function, or a disease associated with compromised pancreatic function, such as diabetes). The threshold amount (e.g., the amount by which a GABA amount or concentration from a subject is lower than a reference standard) which results in a determination that a subject has compromised pancreatic islet function can vary. In some embodiments, the amount of GABA detected in the subject is between about 1% and about 99% lower than a reference standard. In some embodiments, the amount of GABA detected in the subject is between about 1% and about 10% lower, about 5% and about 20% lower, about 15% and about 25% lower, about 20% and about 40% lower, about 30% and about 75% lower, or about 50% and 100% lower than the reference standard. In some embodiments, the amount of GABA detected in the subject is between about 1-fold and 100-fold less than a reference standard (e.g., about 1-fold, 2-fold, 5-fold, 10-fold, 25-fold, 50-fold, 75-fold, or 100-fold lower). In some embodiments, the amount of GABA detected in the subject is more than 100-fold lower than a reference standard.

In some aspects, the disclosure provides a method of treating diabetes comprising administering a therapeutic agent to a subject who has been determined to have compromised pancreatic function by a method described herein. Therapeutic agents for the treatment of diabetes are known in the art, for example as described by Kang (2012) *Korean J Anesthesiol.* 63(3):195-202. Examples of therapeutic agents for treatment of type 1 diabetes include but are not limited to insulin (e.g., natural isolated insulin, recombinant insulin, etc.), insulin degludec, insulin isophane, insulin glulisine, insulin lispro, insulin aspart, glargine, detemir, or any combination thereof. Examples of therapeutic agents for treatment of type 2 diabetes include but are not limited to metformin, a sulfonylurea, a DPP-4 inhibitor, a glucagon-like peptide (e.g., an incretin mimetic), a thiazolidinedione, an alpha-glucosidase inhibitor (e.g., acarbose, miglitol), a sodium glucose transporter (SGLT) 2 inhibitor, or any combination thereof.

Examples

J-Difference Editing: MEGA-PRESS

In vivo detection of low-concentration metabolites such as GABA requires a targeted experiment because the GABA signals in the traditional MR spectrum are overlapped by signals from more concentrated metabolites. J-difference editing is a mechanism to remove the overlapping signals and retain only a signal of interest (e.g., GABA). The removal of confounding signals is achieved by subtracting two slightly different experimental conditions (hence difference editing). MEGA-PRESS is one type of J-difference editing that enhances the GABA signal present in a 1H-MR spectrum.

For example, when used for detection of GABA, the two experimental conditions of MEGA-PRESS differ in how they treat the coupling (typically represented by the symbol J) within the GABA molecule. The majority of signals in the MR spectra produced by the two conditions behave the same. However, the GABA signals (e.g., peaks) of the two conditions behave differently, and thus subtracting the spectra of the two conditions removes confounding signals and retains only the GABA signals (e.g., peaks).

Figure 1B:
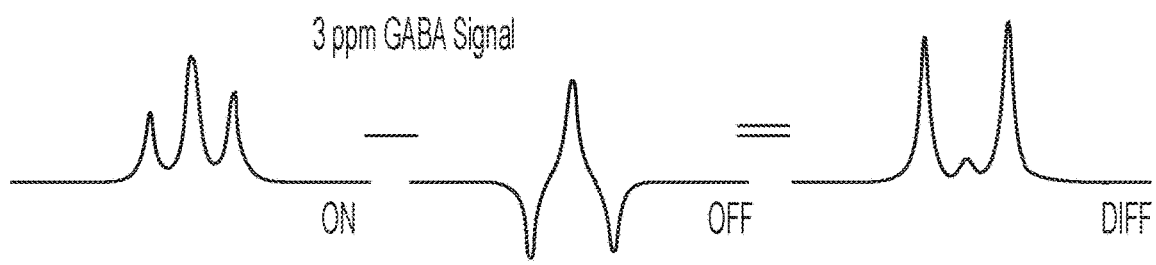

The element that differs between the two experimental conditions of MEGA-PRESS described in this example is the editing pulses, which are selective for GABA. When applied at 1.9 ppm, the editing pulses refocus the evolution of a J-coupling within the GABA molecule, altering the appearance of the GABA signal in the spectrum, as shown in FIGS. 1A-1B. FIG. 1A shows editing pulses applied at 1.9 ppm suppress ("ON") the GABA contribution to the 3 ppm glycine/GABA (GLX/GABA) peaks, which are revealed through the difference ("DIFF") between the "ON" and "OFF" spectra. Note that the "OFF" spectrum is produced in the absence of an editing pulse. FIG. 1B shows that the 1.9 ppm editing pulse enhances the 3 ppm GABA signal (e.g., peaks) present in the "DIFF" spectrum.

Cardiac Triggering and Breath Hold

Acquisition of 1H-MR spectra is generally repeated a large number of times (typically >100) as the single-measurement signal-to-noise ratio (SNR) is high. With repeated acquisitions, the SNR of the acquired data is sufficient for quantification. For MRS of brain tissue, the repetition time (TR) between repeat acquisitions is usually fixed (to ~2 s). Applications of MRS in the body must account for organ movement within the body cavity as a function of the cardiac and respiratory cycle. For example, in pancreas, these motions have two main effects: the position of the pancreas within the body cavity will change with cardiac and/or respiratory motion, and the magnetic field within and around the pancreas will change with cardiac and/or respiratory motion.

To accommodate effects of the cardiac cycle, acquisitions are performed with cardiac and/or respiration triggering, and/or breath-hold, and/or mechanical stabilization (e.g., a rigid band placed around the torso of a subject). The cardiac cycle is determined by fingertip pulse oximeter or ECG connected to the scanner physiological monitoring system. The respiration cycle is determined by respiration sensor connected to scanner. Each TR is triggered following a delay following the cardiac cycle. The breath hold procedure involves instruction to participant to hold breath at a paced interval during which one or more acquisitions may be made.

MRS of GABA in the Pancreas

J-difference-edited MRS of GABA was performed in the pancreas using a modified MEGA-PRESS sequence with PRESS localization and MEGA J-difference editing. Data were acquired using a 16-channel phased-array body coil (e.g., 8 channels placed on the abdomen of the subject and 8 channels placed on the back of the subject in windows of ~32 seconds during which the participant was instructed to breath-hold (exhaled). Editing was performed with 14-ms editing pulses applied at 1.9 ppm in editing-ON scans to refocus evolution of the GABA coupling. Other acquisition parameters included TE=68 ms, a voxel size sufficient to encompass the portion of pancreas being sampled during physiological rhythm associated movement (e.g., respiration, cardiac, peristalsis, etc.) while avoiding digestive tract, 2 kHz spectral width. More than 2,000 data points were acquired. Channels were weighted in a phase-sensitive manner to improve SNR of reconstructed spectra. Spectral registration was used to frequency-and-phase correct the individual transients. Data were Fourier transformed after windowing by a 5-Hz exponential and the difference spectrum was calculated.

In Vivo MRS Detection of GABA

Figure 2:
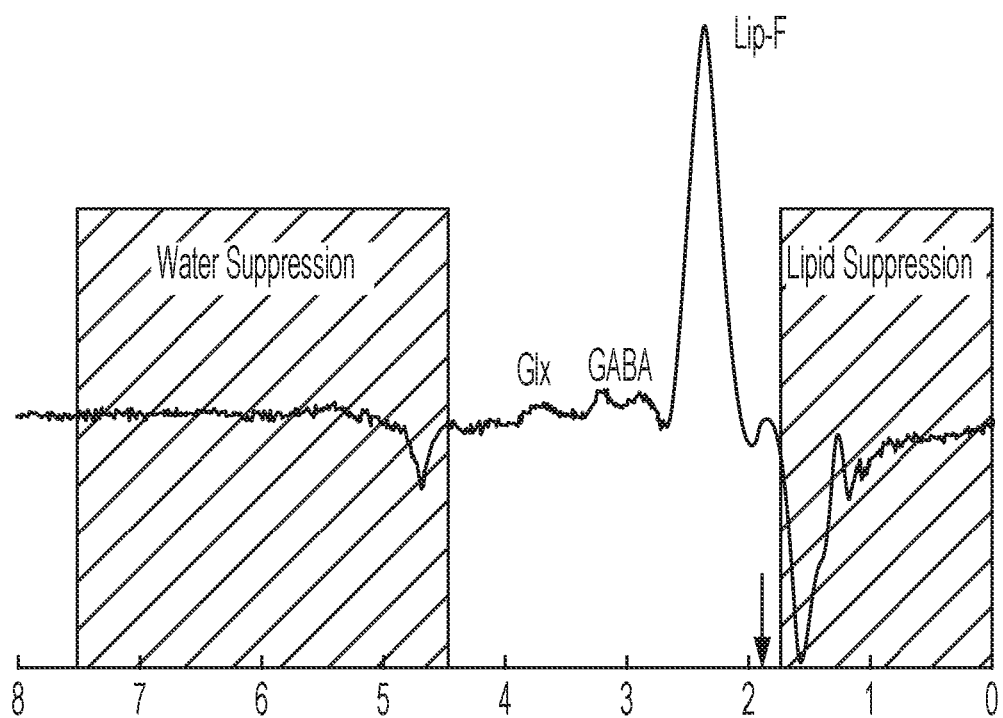
FIG. 2 shows a representative spectrum recorded from healthy human pancreas collected using methods described by the disclosure. Glx: glutamate/glutamine peak; GABA: y-aminobutyric acid peak; Lip-lipid peak.

FIG. 2 shows a representative spectrum recorded from healthy human pancreas collected using methods described as follows. One healthy male subject (aged 32 years, weight 85 kg) was recruited. The subject was positioned supine in a 3.0 T MRI scanner and the subject's abdomen was bound with an elasticated band (30 cm width) to reduce the freedom to move of the abdominal organs, and a 16-channel phased array body coil was placed anterior and posterior to the subject, at the level of the pancreas. Based on T2-weighted anatomical imaging (cardiac triggered FSE with respiratory gating), a 2.5×2.5×5 $cm^3$ voxel was placed so as to include as much pancreas tissue as possible. Shimming of the voxel was performed using Philips 'pencil-beam' voxel-projection method. Chemical-shift-selective water and fat suppression was performed using dual band saturation (Zhu, Ouwerkerk, & Barker, 2010). Acquisition parameters include: MEGA-PRESS sequence; TE/TR 68/2000 ms; 320 averages of 2048 data points, sampled at 2 kHz; 14-ms editing pulses applied alternately at 1.9 ppm, to refocus evolution of the coupling to the GABA signal at 3 ppm, and 7.46, allowing the GABA coupling to evolve. Coil combination was performed based on the amplitude and phase of the unsuppressed water signal from each channel of the 16-channel torso coil. 3 Hz exponential line broadening was applied prior to Fourier transformation and display of the spectrum in FIG. 2. Data indicate selective positioning of receiver arrays combined with J-difference editing allows for detection of GABA at 3 T in pancreas. Co-editing of additional predicted resonances from Glx (due to coupling to Glx signals around 2 ppm) and lipid signal Lip-F was also performed (FIG. 2).

What is claimed is:

1. A method for quantifying GABA in a subject, the method comprising:
   (i) acquiring a plurality of proton magnetic resonance (1H-MR) spectra from a multi-channel receiver array placed around the torso of a subject;
   (ii) performing subtractive J-difference editing on the 1H-MR spectrum obtained from each channel of the receiver array to produce edited difference spectra;
   (iii) generating at least one edited difference spectra having a peak at 3.0 ppm by selecting from one or more channels of the receiver array; and,
   (iv) quantifying GABA concentration in the pancreas of the subject based upon the 3.0 ppm peak amplitude of the difference spectra selected in (iii) relative to at least one internal reference signal obtained from the receiver array.

2. The method of claim 1, wherein the plurality of 1H-MR spectra are acquired using a magnetic field strength between 0.2 and 12 Tesla (T).

3. The method of claim 1, wherein acquisition of the plurality of 1H-MR spectra comprises a point-resolved spectroscopy (PRESS) acquisition sequence.

4. The method of claim 3, wherein the echo time (TE) of the PRESS acquisition sequence is between 50 ms and 100 ms.

5. The method of claim 1, wherein acquisition of the plurality of 1H-MR spectra comprises chemical-shift-selective editing pulses wherein the chemical-shift-selective editing pulses are applied at a chemical shift between −2.7 ppm and −2.8 ppm relative to the internal reference signal.

6. The method of claim 5, wherein the chemical-shift-selective pulses comprise a Mescher-Garwood (MEGA) refocusing pulse sequence, wherein each of the chemical-shift-selective pulses has a duration between 10 and 25 ms.

7. The method of claim 1, wherein the acquiring step is repeated between 100 and 1000 times.

8. The method of claim 1, wherein the subject is holding their breath during each acquisition of 1H-MR spectrum.

9. The method of claim 1, wherein the multi-channel receiver array comprises at least four channels, at least eight channels, or at least 16 channels.

10. The method of claim 1, wherein at least four channels of the multi-channel receiver array are positioned to acquire spectra from a position anterior to the subject.

11. The method of claim 1, wherein at least four channels of the multi-channel receiver array are positioned to acquire spectra from a position posterior to the subject.

12. The method of claim 1, wherein at least one channel of the multi-channel receiver array acquires 1H-MR spectra from a voxel within the pancreas of the subject, wherein the voxel ranges from about 1 cm$^3$ to about 250 cm$^3$.

13. The method claim 1, wherein the subject has a mechanically-restrained pancreas.

14. The method of claim 1, wherein the concentration of GABA (cGABA) is quantified using the following equation:

$$c_{GABA} = c_{ref} \frac{S_{GABA}}{S_{ref}} R\kappa$$

where $C_{ref}$ is the concentration of the reference signal, $S_{GABA}$ and $S_{ref}$ are the signal integrals of the GABA and reference signals respectively, R is a term to correct for differential relaxation of GABA and reference signals and κ is a constant to adjust for editing efficiency, wherein the internal reference signal is derived from water, creatine, or glutamate.

15. A method for identifying compromised pancreatic islet function in a subject, the method comprising:
   quantifying a GABA concentration of the subject using the method of claim 1;
   comparing the GABA concentration in the subject to a reference standard; and,
   determining that pancreatic islet function of the subject is compromised if the concentration of GABA in the subject is lower than the reference standard.

16. The method of claim 15, wherein the reference standard comprises a GABA concentration obtained from a healthy subject, for example a subject that does not have compromised pancreatic islet function.

17. The method of claim 15, wherein the method further comprises administering a therapeutic agent to the subject if the subject has been determined to have compromised pancreatic islet function.

18. A method for treating diabetes in a subject, the method comprising administering a therapeutic agent to the subject, wherein the subject has been determined to have compromised pancreatic islet function by the method of claim 15, wherein
   (i) the diabetes is type 1 diabetes, and wherein the therapeutic agent is insulin, insulin degludec, insulin isophane, insulin glulisine, insulin lispro, insulin aspart, glargine, detemir, or any combination thereof; or
   (ii) the diabetes is type 2 diabetes, and wherein the therapeutic agent is metformin, a sulfonylurea, a DPP-4 inhibitor, a glucagon-like peptide, a thiazolidinedione, an alpha-glucosidase inhibitor, a sodium glucose transporter (SGLT) 2 inhibitor, or any combination thereof.

* * * * *